(12) United States Patent
Freitag

(10) Patent No.: US 6,171,870 B1
(45) Date of Patent: Jan. 9, 2001

(54) ANALYTICAL TEST DEVICE AND METHOD FOR USE IN MEDICAL DIAGNOSES

(75) Inventor: Helmut E. Freitag, Birmingham (GB)

(73) Assignee: Spectral Diagnostics, Inc., Toronto (CA)

(*) Notice: Under 35 U.S.C. 154(b), the term of this patent shall be extended for 0 days.

(21) Appl. No.: 09/130,164

(22) Filed: Aug. 6, 1998

(51) Int. Cl.$^7$ .................................................. G01N 33/543
(52) U.S. Cl. .......................... 436/518; 436/514; 436/164; 436/165; 436/69; 435/4; 435/7.1; 435/7.5; 435/7.9; 435/7.92; 435/287.1; 435/287.2; 422/56; 422/57; 422/58; 422/61
(58) Field of Search ...................... 435/5, 7.1, 7.2, 435/7.24, 7.29, 7.92, 287.2, 288.2, 6, 91.2, 4, 7.5, 7.9; 436/514, 516, 518, 164, 165, 69; 422/56, 57, 58, 61, 72, 82.06; 250/341

(56) References Cited

U.S. PATENT DOCUMENTS

| | | |
|---|---|---|
| 4,477,575 | 10/1984 | Vogel et al. . |
| 4,753,776 | 6/1988 | Hillman et al. . |
| 4,774,192 | 9/1988 | Terminiello et al. . |
| 4,861,711 | 8/1989 | Friesen et al. . |
| 4,933,092 | 6/1990 | Aunet et al. . |
| 4,956,275 * | 9/1990 | Zuk et al. .................................. 435/7 |
| 4,987,065 | 1/1991 | Stavrianopoulos et al. . |
| 5,075,078 | 12/1991 | Osikowicz et al. . |
| 5,079,142 | 1/1992 | Coleman et al. . |
| 5,079,143 * | 1/1992 | Coleman et al. ................... 435/7.92 |
| 5,096,809 | 3/1992 | Chen et al. . |
| 5,110,724 | 5/1992 | Hewett . |
| 5,120,643 | 6/1992 | Ching et al. . |
| 5,135,716 | 8/1992 | Thakore . |
| 5,141,850 | 8/1992 | Cole et al. . |
| 5,144,890 | 9/1992 | Korhonen . |
| 5,290,678 | 3/1994 | Jackowski . |
| 5,300,779 * | 4/1994 | Hillman et al. ....................... 250/341 |
| 5,591,645 | 1/1997 | Rosenstein . |
| 5,747,274 * | 5/1998 | Jackowski ............................ 435/7.94 |
| 5,811,296 * | 9/1998 | Chemelli et al. .................. 435/287.2 |
| 5,885,526 * | 3/1999 | Chu ........................................ 422/56 |
| 5,912,134 * | 6/1999 | Shartle ............................... 435/7.24 |
| 5,928,880 * | 7/1999 | Wilding et al. ........................ 435/7.1 |
| 5,939,331 * | 8/1999 | Burd et al. ........................... 436/518 |
| 5,961,923 * | 10/1999 | Nova et al. .......................... 422/68.1 |
| 5,985,675 * | 11/1999 | Charm et al. ........................ 436/514 |

OTHER PUBLICATIONS

Galpre and Milstein et al., 1977, Nature, 266:550–2.

\* cited by examiner

*Primary Examiner*—Christopher L. Chin
*Assistant Examiner*—Minh-Quan K. Pham
(74) *Attorney, Agent, or Firm*—Klauber & Jackson (57) ABSTRACT

An analytical test device is described for the immunochromatographic determination of the presence of one or more analytes in fluid samples. The device is configured such that the sample is allowed to enter the detection zone simultaneously from many different directions, eliminating stagnation of the flow of the sample. By selection of the porous substrate, the device also allows for the separation of red blood cells from plasma, providing a rapid test for one or more analytes in a sample of whole blood. The device of the present invention may measure more than one analyte simultaneously from a single sample, either by having multiple immunochromatographic pathways fed by a single sample, or multiple analytes detected in the same pathway by way of multiple capture antibodies.

70 Claims, 8 Drawing Sheets

ANALYTICAL TEST DEVICE AND METHOD FOR USE IN MEDICAL DIAGNOSES

FIELD OF THE INVENTION

This invention relates to analytical test devices and methods useful for analytical assays to determine the presence of analytes in fluid samples. It is especially useful for determining the presence of cardiac analytes in whole blood, although it is not so limited.

BACKGROUND OF THE INVENTION

This invention can be utilized for many diagnostic purposes as well as for following the course of mammalian diseases and therapeutic treatments. It is applicable to many mammalian body fluids such as whole blood, serum, plasma and urine. Although this invention will be principally discussed as applied to detecting cardiac analytes it may also be applicable to other fields where antigen/antibody or equivalent reactions are utilized.

It may, for instance, be employed for pregnancy or fertility testing utilizing antibodies to human chorionic gonadotropin (LCG) or leutinizing hormone (LH) as well as for detection and/or measuring a wide variety of analytes in blood and other body fluids.

A number of immunoassay procedures have recently been developed which utilize reactions taking place on dry porous carriers such as cellular membranes through which samples to be analyzed can flow by capillary action, the reaction products being detectable either visually or with an instrument such as a reflectometer. While not so limited, these procedures generally involve antigen/antibody reactions in which one member of the reactive pair is labelled with a detectable label. Typically, the label is an enzyme label or a particulate direct label, for instance a sol label such as gold. The art is well aware of many useful labels and their method of operation.

Typical immunochromatographic devices of this nature are described in several United States and foreign patents. For example, U.S. Pat. No. 4,861,711 describes a device in which an analyte is detected by antigen/antibody reactions taking place in a series of coplanar membranes in edge to edge contact. Other devices are described in U.S. Pat. Nos. 4,774,192; 4,753,776; 4,933,092; 4,987,065; 5,075,078; 5,120,643; 5,079,142; 5,096,809; 5,110,724; 5,144,890; 5,290,678; 5,591,645; 5,135,716. All of these patents describe laminated structures.

Devices including cellular porous membranes such as those described in the above identified patents are often difficult to manufacture because they are multi-layer and require several layers of porous materials and filtration strips to insure accurate results.

For detection of cardiac analytes in whole blood, it is necessary to remove red blood cells so that they will not interfere with visualizing or otherwise detecting the colored reaction products normally produced in such immunoassay reactions.

Immunoassay devices when employed to detect cardiac analytes in whole blood utilize labelled antibodies which react with these antigens to produce detectable products. One widely utilized method for such diagnostic or analytical procedures utilizing antigen/antibody reactions employs a labelled detector antibody which reacts with one epitope on the antigen to form a labelled antibody/antigen complex formed in a detection zone of a porous membrane strip. The complex moves along the membrane by capillary action until it contacts a fixed line containing a capture antibody with which it reacts at another epitope on the antigen to concentrate and form a detectable reaction product. Typically, the product is visibly detectable because it is colored. With some constructions, the color is apparent to the naked eye. In more sophisticated devices, the presence or concentration of the antigen may be determined by measuring the intensity of the produced color or other property of the product with a suitable instrument, for example an optical sensor. The method is utilized in several devices used to detect cardiac analytes in whole blood. In all of these devices, it is necessary to prevent red blood cells from entering the color development or capture area because they interfere with proper visualization of the colored reaction product because of the intense hue of the cells.

Much effort has been expended to prevent such interference. As a result, products of this nature heretofore proposed for analysis of whole blood include some means, such as a type of filter to remove the red blood cells and form a plasma, so that there is no interference with the visibility of the color which is produced.

U.S. Pat. No. 5,135,716 utilizes an agglutinating agent to assist in the separation of red blood cells. Other patents describe the use of paper or plastic filters.

The use of glass fiber fleece is described in U.S. Pat. No. 4,477,575 to filter the red blood cells. Glass fiber fleece, however, simply adds another layer to the device. The principal difficulties arise from the problems of accurately placing several layers of thin flexible strips in proper registry in a laminar structure while at the same time retaining the sample placement zones, reaction zones and other areas of the membrane strips in proper communication with each other. The problems are further complicated by the difficulties of placing the completed membrane in or on a proper platform which is often a hollow casing with separable upper and lower members including fixed pillars and slots to prevent the membrane from moving and to retain selected membrane areas in proper position relative to viewing windows and other openings in the casing.

As a general rule, diagnostic devices such as those discussed above are often described as having an application zone to which the sample to be analyzed is added. The sample flows to a detection zone. The detection zone carries a mobile, labelled antibody to the analyte sought. If the analyte is present, a labelled antibody/analyte complex is formed which reacts with a fixed, i.e., immobilized capture antibody in a capture zone to form a detectable product, usually one which is colored and visible to the naked eye.

It sometimes happens that the labelled antibody/analyte complex forms quite readily but does not sufficiently combine with capture antibody to produce an easily detectable signal. This might happen if no sufficient amount of complex contacts capture antibodies or contacts them in a configuration which is not optimum for forming a detectable reaction product. Other possible problems are insufficient incubation time or low antibody affinity.

These difficulties may be avoided by taking advantage of the biotin/avidin or biotin/streptavidin reaction or analogous reactions well known to the skilled artisan. These reactions are often used to increase the sensitivity of the diagnostic procedure.

In one application of this process, two antibodies are removably deposited in the detection zone and streptavidin is immobilized in the capture zone. The detector antibody is labelled, preferably with a metal such as gold, and reacts with one epitope on the analyte. The other antibody which is labelled with biotin reacts with another epitope on the analyte. The antibody mixture may be considered as a reagent system for use in detecting the presence of the analyte. If analyte is present, a complex containing labelled detector antibody/analyte/biotin labelled detector antibody will form in the detection zone. The complex will move through a cellular membrane by capillary action to the capture zone. When the complex reaches the immobilized streptavidin in the capture zone, the streptavidin binds to the biotin and concentrates the complex in a small area to form a detectable reaction product.

There are several known variations of this reaction. For example, the detection zone may contain a biotin labelled antibody together with streptavidin labelled with a colored label such as gold. The complex which forms and moves into the capture zone is an analyte/biotin labelled antibody/streptavidin gold-labelled complex which will move to the capture zone and concentrate in the capture zone by reaction with a capture antibody to form a detectable reaction product.

The above identified procedures have generally been described to involve reactions taking place on an elongated, rectangular, laminated device with the sample application zone at one end associated with some type of filter layer. The sample, after filtration, contacts a mobile, labelled specific binding reagent in a detection zone to form a complex which moves along a cellular membrane to a distally placed specific binding reagent, i.e., the capture reagent which is immobilized in a line across the membrane. The complex reacts with the reagent and is concentrated along the reagent line to become visible.

Typically, the sample to be analyzed is placed in the application zone by the addition of several drops to the center of the zone or by dipping the application zone into a small volume of the sample.

There are a number of problems with this configuration, especially when the goal is high sensitivity and the result should be visible within only a few minutes.

High sensitivity can be achieved, for instance, by a capture line in a capture zone having a small width, as compared to the width of the detection zone, so that the amount of labelled reaction product is captured within a small capture area and thereby give a more intense signal color.

Further, the sensitivity can be increased as more labelled volume moves across the capture line during the test procedure. The more labelled volume is needed, however, the greater the area of the detection zone must be.

If this area has the form of an elongated channel and is increased by simply increasing the length thereof, the consequence is a considerable increase in test time, because the velocity of the moving liquid front slows down exponentially with the total distance wetted.

Other shapes of this area (e.g. with a higher ratio of width to length) leading to a large width detection zone and a small width capture zone channel have the disadvantage of creating stagnation regions where there is little or no flow. In extreme cases significant amounts of the sample may never become involved in the reactions which form the detectable product.

BRIEF SUMMARY OF THE INVENTION

The solution to these problems as explained herein is that the sample is allowed to enter into the detection zone simultaneously from many different directions and the detection zone is designed in a way that the resulting flow from the different directions all points to the entrance of the capture zone channel and all distances from entering the detection zone to said entrance are essentially the same.

This invention alleviates many of the problems aforesaid by providing a device which may be small enough to be hand held, although not necessarily so, and provides for rapid and efficient flow of the fluid to be analyzed. Although its presently preferred utility is for the analysis of whole blood to diagnose for the presence of cardiac analytes, it may be adapted to test for the presence of other components in a fluid such as a body fluid carrying an antigen which will form a complex with an antibody which may thereafter be detected, for example in a sandwich assay with another antibody.

Rapid and efficient flow of the fluid to be analyzed can be achieved by configuring the porous channels so that there is little or no opportunity for stagnation and so that the fluid enters a detection zone from a sample circulation channel from a multitude of points. The detection zone is designed so that the resulting front of the fluid moves in the direction of the entrance end of the capture zone.

A particular advantageous aspect of the invention when employed to whole blood is the selection of a porous substrate which chromatographically separates red blood cells from plasma. The chromatographic separation is of particular importance compared to filtration of particulate material because actual filtration may clog the cells of the media and impede or even stop flow. Moreover, as discussed above, filtration normally requires additional layers. In chromatographic separation, however, the particulate material continues to flow although at a slower rate than the carrier fluid so that there is little or no impedance of flow. With other biological samples chromatographic separation may not be necessary.

Another important feature of the invention, as will be explained below, is that all flow stops at a preselected point because the entire volume of the sample pathway in the porous carrier is wetted, and particulate material such as red blood cells does not interfere with the detection of the detectable reaction product.

BRIEF DESCRIPTION OF THE DRAWINGS

FIGS. 1 and 2 represent attempted configurations to increase the labelled volume or, respectively, to increase the ratio of widths of the detection zone over the capture zone. FIG. 3 is the usual standard configuration in which the width of the porous carrier, i.e. the membrane, is uniform throughout its length.

GLOSSARY

The following terms are intended to have the following general meaning as they are used herein.

"Dry porous carrier" and "dry porous carrier layer" refer to a cellular product through which the sample to be analyzed can move by capillary action. As will be seen by the figures and understood by the description of the invention, the dry porous carrier (layer), which in this art is often referred to as a membrane, is configured by closing off some of the porous areas so that the fluid to be analyzed moves along defined pathways through selected channels.

"Top layer or plate" is a layer in the analytical test device which is configured to cooperate with the dry porous carrier layer when the two are placed in registry to provide pathways which control the direction of flow of the sample to be analyzed through the device.

"Antigen" is a molecule which, in an animal, induces the formation of an antibody. The devices of this invention are useful for determining the presence of antigens in a fluid. They are especially useful for analyzing body fluids particularly whole blood, serum, plasma and urine. Antigens are often referred to as "analytes".

"Cardiac analytes" are analytes which are released into the blood as a result of cardiac tissue deterioration.

"Channel" is any formed conduit through which the fluid under analysis flows in the analytical test device. A channel may be formed in the top layer or in the porous carrier layer itself. Since the top layer is generally a rigid plastic such as a polyacrylate or polymethacrylate, a channel may be formed by molding, stamping, machining or any equivalent process. In the porous layer, the channels may be formed by stamping the desired configuration into the layer. They may also be designed into the porous layer by forming non-porous boundaries with wax or ink. Channels are said to be in an operative communication when a fluid in one channel flows directly into another.

"Semicircular", as the word is used herein is not limited to one half of a circle, but generally refers to a circle area where a sector has been removed or to this sector itself.

"Circumscribed", as the word is used herein is not limited to an arcuate channel surrounding and conforming to a semicircular area of a porous membrane. The term includes—as will be apparent as this description continues—other configurations in which a sample circulation channel conforms with the border of one or more detection zones of other configurations, for instance when the area of the carrier is polygonal or forms part of a polygon.

"Essentially" is a term used in connection with the distances between the points of sample entry into the detection zone and the entrance end of the capture zone channel. These distances should be as similar as possible. Obviously, a semicircular area on the carrier to which an arcuate sample circulation channel conforms is a highly preferred configuration because all resulting distances between the arcuate border of the detection zone and the entrance end of the capture zone channel are the same.

"Rapid" means that a detectable product forms within a sufficiently short period of time, e.g. within about 5 to about 15 minutes, to permit the medical attendant to draw meaningful and useful conclusions.

"Efficient" means that a detectable product can be formed with a low volume of fluid, e.g. a few drops of whole blood (from about 10 $\mu$l to about 80 $\mu$l), utilizing small amounts of reagents even when the antigen is present in very low concentrations as is usually the case with the cardiac analyte troponin I.

Figure 1:
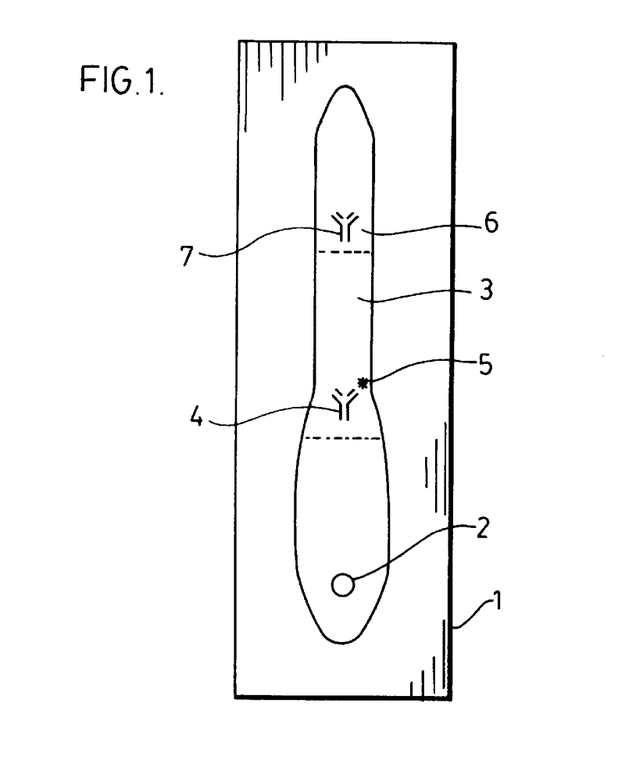
FIGS. 1, 2 and 3 are representations of the prior art.
Figure 2:
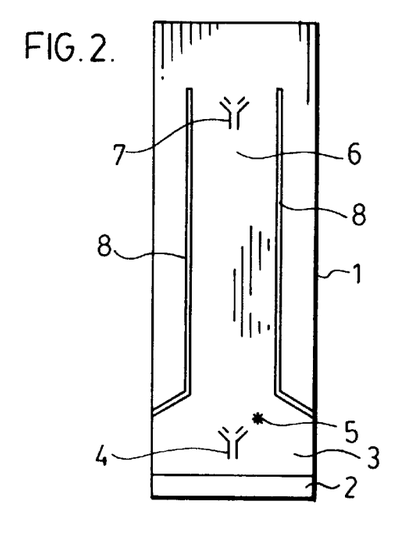
Figure 3:
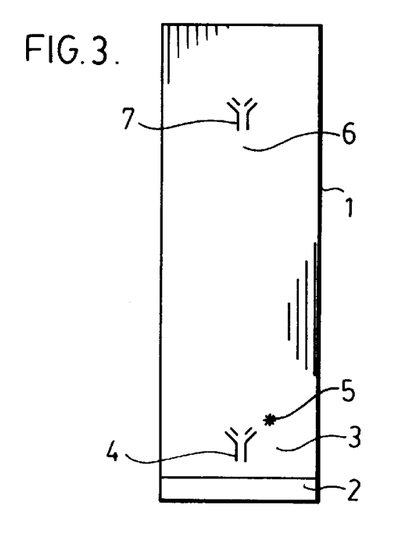

FIGS. 1, 2 and 3 are prior art devices. In the figures, like numbers have similar meanings.

FIG. 1 is a view of one prior art device configured in an attempt to avoid the problems described above. In the figure, 1 is a porous cellular membrane such as nitrocellulose. The sample to be analyzed is added in area 2.

The detection zone 3 contains a mobile reactive reagent, for example a detection antibody 4 for troponin I in a plasma carrier. The antibody 4 is labelled with a label 5 such as gold.

For convenience, the devices of FIGS. 1, 2 and 3 are shown as unilayer membranes. However, in practice most of them would have a series of filtration layers over the area 2 so that only plasma carrying analyte would reach area 2. Alternatively, the red blood cells in the sample can be removed by clotting to form a serum. However, this is a separate step performed exterior of the device and normally requires separate filtration of the mixture of clotted blood cells with the serum before undertaking the test.

If the analyte is present, it will react with the labelled antibody 4 to form a labelled antibody/analyte complex which will move with the plasma by capillary action into capture zone 6 where it will react with capture antibody 7 fixed and immobilized in the capture zone 6. As a result, the labelled antibody/analyte complex will form a detectable reaction product in the area of capture antibody 7. Normally, antibody 7 is fixed in a line traversing the capture zone 6 and the reaction product will be visible to the naked eye. If the label is gold the line will be red to purple.

The problem which arises with a configuration such as shown in FIG. 1 is that the plasma carrying the analyte travels in all directions away from zone 2. A portion will travel towards the detection zone 3 and the capture zone 6. However, another portion will travel in the opposite direction and will thus never reach the capture zone 6.

FIG. 2 shows a prior art device employing flow barrier means (8) to increase the length of the pathway through which the sample must flow. The problem with this device is that the dead spots at the top periphery of the detection zone 3 create areas of stagnant flow.

FIG. 3 shows an elongated rectangular shaped porous substrate on which the same reactions take place as on FIGS. 1 and 2. There is no fluid stagnation and none of the fluid is trapped. The principal problem with this standard device of FIG. 3 is that if the device is too short, not enough of the labelled volume contacts and reacts with the capture antibody to produce a sufficient quantity of reaction product to be detectable. If the device is too long, too much time will pass before the test result is available.

DETAILED DESCRIPTION OF THE INVENTION

As discussed above, the device of this invention may be employed to analyze a variety of liquid biological samples for the presence of an antigen. It is presently contemplated that the device will find its principal utility for the diagnosis of whole blood for the presence of cardiac analytes such as troponin I (TNI), troponin T, myoglobin, creatine kinase MB (CK-MB), myosin light chain, carbonic anhydrase, fatty acid binding protein, glycogen phosphorylase BB, actin and any of a host of other known analytes which are found in the blood as cardiac tissue deteriorates following an ischemic event such as angina or myocardial infarction. Accordingly, as an illustration of its breadth, the invention will be principally described as utilized in the diagnosis of cardiac events.

The prior art and its deficiencies have been discussed above in general and also in connection with FIGS. 1, 2 and 3.

Figure 4:
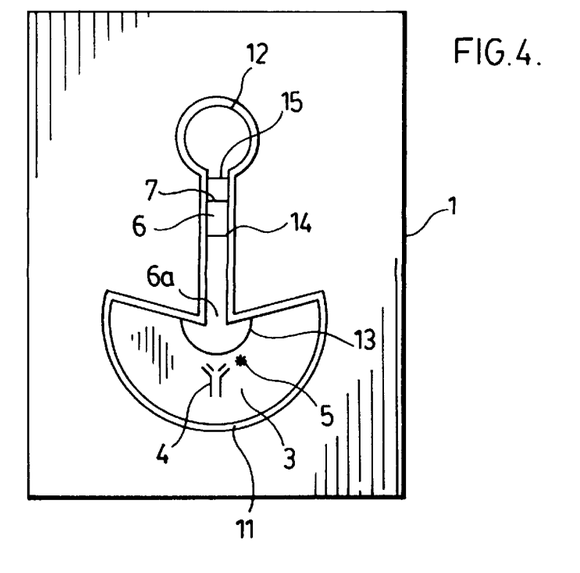
FIG. 4 shows a membrane configuration of a device of the invention suitable for detecting one or several analytes with one semicircular detection zone and one narrow capture zone channel. The border of the semicircular detection zone will connect to a sample circulation channel.

FIG. 4 illustrates a dry porous carrier layer 1 of the invention configured for the analysis of whole blood for one analyte or a plurality of analytes by reactions between the analyte(s) and antibody pairs which react with different epitopes on the analyte in the classical antigen/antibody reaction utilizing polyclonal or monoclonal antibody pairs, one member of the selected pair being labelled.

The figure shows carrier layer 1 in which the porosity of a selected section of the layer has been destroyed to leave only one porous area defining semicircular detection zone 3 with a border 11 and capture zone channel 6 which is closed at terminal end 12.

This membrane 1 which is preferably nitrocellulose or equivalent material chromatographically separates red blood cells to form a red blood cell front 13 and a plasma front 14 downstream thereof.

The detection zone 3 contains labelled detection antibody 4 and 5 which reacts with the analyte, if present, to form a labelled antibody/antigen complex.

Although, for convenience, only one antibody is shown, the detection zone 3 may contain several labelled antibodies.

The labelled antibody 4 is mobile, i.e., it is movably deposited in the detection zone 3 by any of several known means so that the labelled antibody/analyte complex once formed is free to move downstream into the capture zone channel 6 for reaction with the capture antibody 7 fixed transverse of the capture zone channel 6 to form a detectable reaction product.

Again, for convenience, only one capture antibody line 7 is shown, but there may be a plurality of such lines, one for each analyte to be detected.

Capture zone channel 6 may optionally contain a product 15 which reacts with any substance normally present in blood, plasma, serum or other sample to produce a visible control product. The use of a control reaction is optional, but is preferred.

Figure 5:
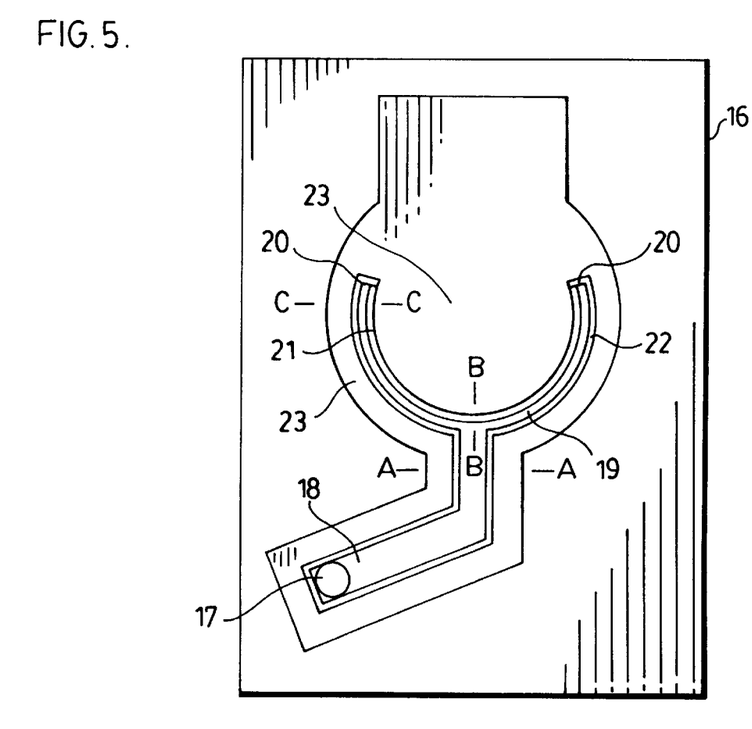
FIG. 5 shows the configuration of the lower surface of the top layer of a device of the invention suitable for use with the membrane of FIG. 4.

FIG. 5 shows the configuration of the lower surface of the top layer 16 which will be brought into registry with the membrane 1 of FIG. 4 to provide a device of the invention.

The top layer 16 has a through hole 17 for application of the sample. It is in operative communication with sample delivery channel 18 which communicates with sample circulation channel 19. Sample circulation channel 19 is shown in an arcuate configuration in order to conform with the border 11 of the semicircular detection zone 3 of FIG. 4.

Sample circulation channel 19 is closed at both ends 20. It is formed with inner wall 21 and outer wall 22 and is surrounded by a capillary trap 23 which functions to assure that the flow of sample is into the detection zone 3 of FIG. 4 at all points of border 11, and then into the capture channel 6 at its entrance end 6a.

Figure 6:
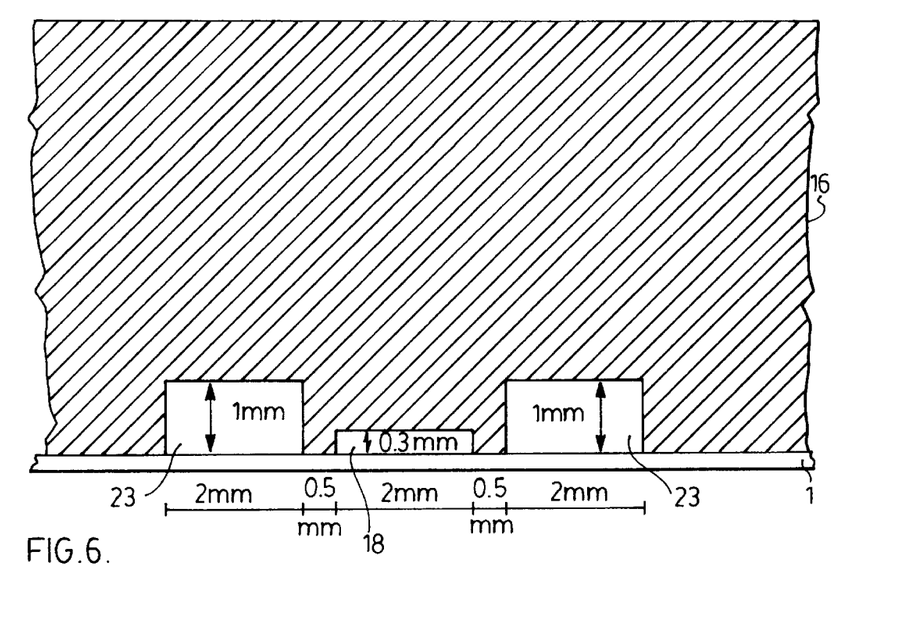
FIGS. 6, 7 and 8 are sectional views along the lines A—A, B—B and C—C of FIG. 5.
Figure 7:
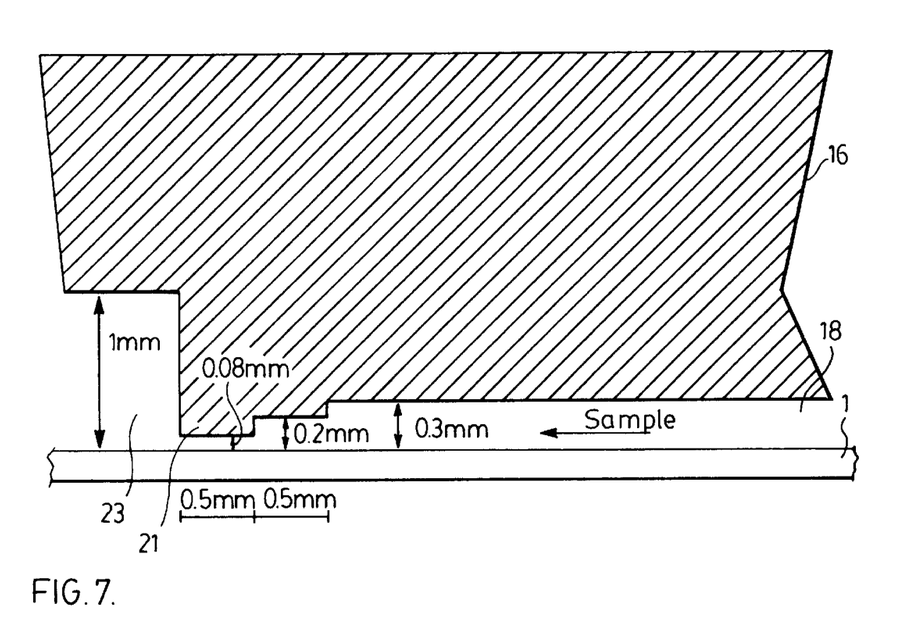
Figure 8:
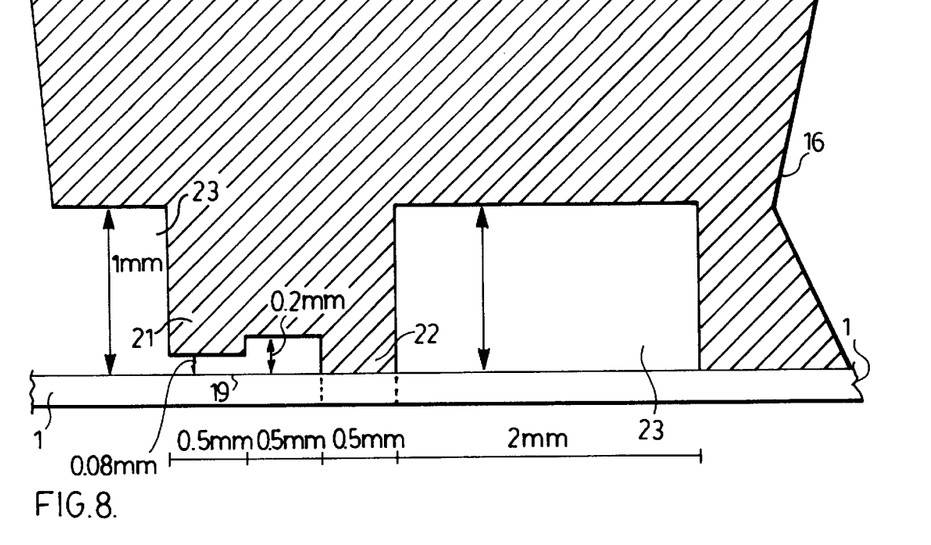

FIGS. 6, 7 and 8 are sectional views along the lines A—A, B—B and C—C, respectively, of FIG. 5. Like numerals have the same meaning. Dimensions [mm] are merely for illustration. Dimensions do not fit to scale.

Figure 9:
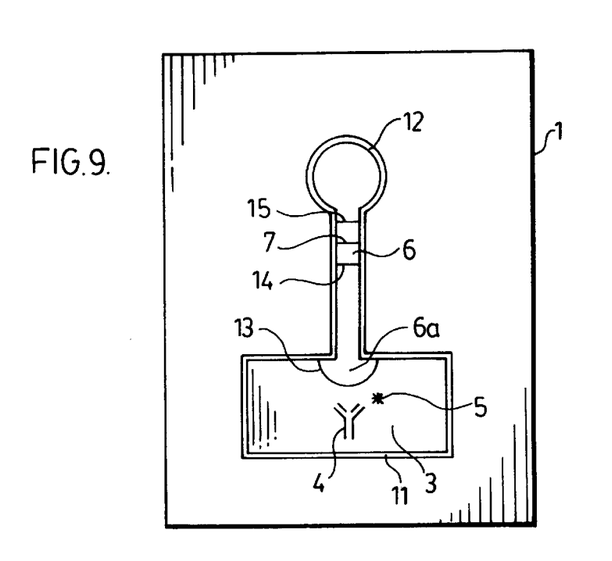
FIG. 9 shows a membrane configuration of a device of the invention for detecting one or several analytes with one rectangular detection zone and one narrow capture zone channel.
Figure 10:
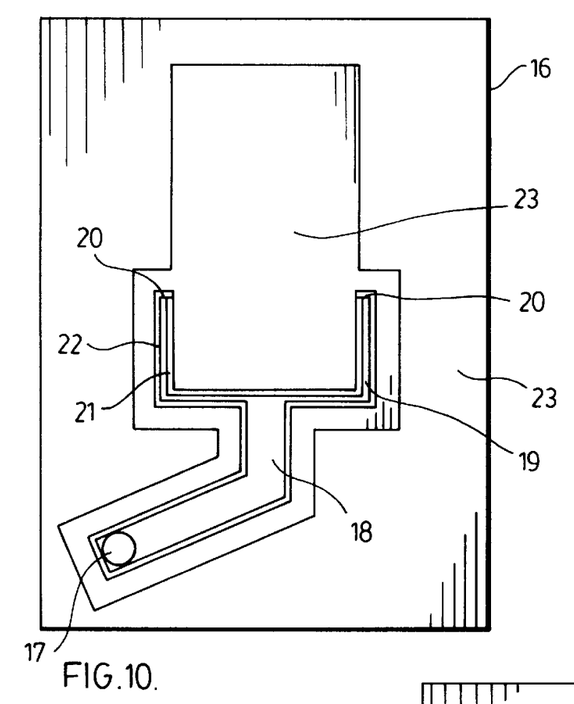
FIG. 10 shows the configuration of the lower surface of the top layer of a device of the invention suitable for use with a membrane of FIG. 9.

FIGS. 9 and 10 are similar to FIGS. 4 and 5 except that the detection zone 3 is rectangular in configuration and the sample circulation channel 19 which circumscribes the border 11 is similarly rectangular. As with FIGS. 4 and 5 the device is shown with one mobile, labelled, detection antibody 4 and 5 and one fixed capture antibody 7.

The device of FIGS. 9 and 10 can be employed to detect one or more than one analyte provided that there is no substantial amount of cross reaction.

Figure 11:
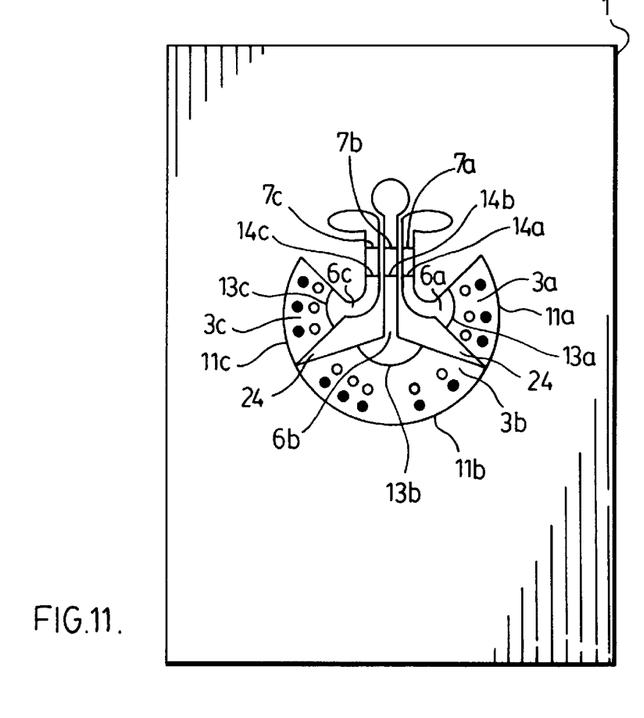
FIG. 11 shows the configuration of a presently preferred membrane of the invention suitable for the detection of three different analytes via the biotin/streptavidin route.

FIG. 11 shows the configuration of a presently preferred membrane 1 of the invention in which the biotin/streptavidin reaction is utilized to diagnose a whole blood sample for the presence of three analytes. The configuration of the channels in the top layer can be readily devised from the foregoing explanation and the explanation which comes after. In the figure like numerals have the same meaning as in the other figures. The design may be employed to ascertain the presence of the analytes myoglobin, troponin I or T and CK-MB in one small sample.

The membrane 1 is formed with three distinct pathways, one for each analyte leading from the borders 11a, 11b and 11c of three separate detection zones 3a, 3b and 3c. The detection zones are separated by blocking segments 24. The whole operative area is configured so as to provide three detection zones 3a, b and c in operative communications at their borders 11a, 11b and 11c with the sample circulation channel 19 on the lower surface of the upper layer 16 of the device (not shown in the figure). The detection zones 3a, 3b and 3c are in operative communication with the corresponding entrance ends 6a, 6b and 6c of the respective capture zone channels.

The detection zone 3a contains two labelled antibodies, e.g. a biotin labelled antibody to CK-MB and a gold labelled antibody to CK-MB.

Generally, in FIG. 11 black circles stand for gold labelled antibodies while white circles stand for biotin labelled antibodies. No reference numerals are given for these detector antibodies in order not to clutter this figure.

As an example of the separation of the plasma from red blood cells during the operation of the device of FIG. 11, the red blood cell front in each of the three detection zones 3a, 3b, and 3c is shown as 13a, 13b, and 13c, respectively; the location of the respective plasma fronts are shown as 14a, 14b, and 14c, respectively.

If CK-MB is present in the sample, the complex which forms will enter the capture channel at entrance 6a to ultimately react with streptavidin at the streptavidin line 7a to produce a visible product.

Analogous reactions take place with other analytes such as troponin I or troponin T and with myoglobin in the separate pathways shown in the figure.

FIGS. 12 through 16c are provided to further explain the invention and to show its versatility.

The same or other analytes may be similarly detected with conventional antigen antibody reactions.

Figure 12:
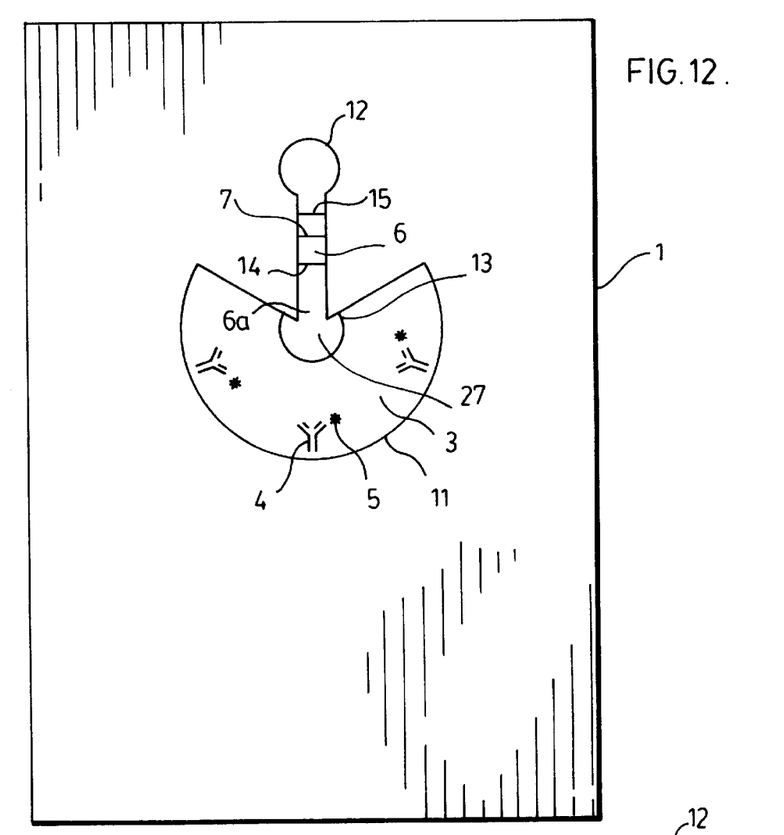
FIGS. 12 and 13 show the configurations of alternative porous membranes with one and three fluid pathways, respectively.

FIG. 12 illustrates a porous carrier layer 1 of the invention configure for the analysis of whole blood for one analyte such as troponin I.

The figure shows the porous carrier layer 1 in which the porosity of the layer has been destroyed in some areas to define detection zone 3 and capture zone channel 6 which is closed at terminal end 12.

The membrane 1 which is preferably nitrocellulose or equivalent material chromatographically separates red blood cells to form a red blood cell front 13 and a plasma front 14.

In this embodiment of the invention, the detection zone contains a labelled detection antibody 4 which is constructed with label 5. The antibody reacts with the analyte, if present, to form a labelled antibody/antigen complex.

The labelled antibodies 4, 5 are mobile, i.e., they are movably deposited by any of several known means in the detection zone 3 so that the labelled antibody/analyte complex once formed is free to move downstream into the capture zone channel 6 for reaction with a capture antibody at line 7 fixed transverse of the capture zone channel 6 to form a detectable reaction product.

Capture zone channel 6 may optionally contain a product 15 which reacts with any substance normally present in blood, plasma, serum or other body fluid to produce a visible product. The use of a control reaction is optional, but is preferred so that the operator will know that sufficient blood or other fluid has been applied to the device to permit diagnostic reactions to take place.

It will be noted that detection zone 3 and capture zone channel 6 are in operative communication, i.e., fluid in detection zone 3 will flow by capillary action directly into capture zone channel 6 through the entrance end 6a.

It will also be noted that the detection zone 3 has a semicircular geometry and thus an arcuate border 11. The center of this are where detection zone 3 is in operative communication with the capture zone channel 6 can be considered a second or opposite end 27 of the detection zone 3 through which fluid can flow into the entrance end 6a of the capture channel 6. As a result of this configuration, every point on the border 11 is equidistant from the entrance end 6a of the capture zone channel 6 and all of the fluid in the detection zone channel flows uniformly into the capture zone channel 6 with successive segments of the sample reaching the entrance end 6a at substantially the same time. This uniformity of flow from several directions will be more clearly understood in connection with the description of the top layer which appears below.

A major feature of the device of this invention is that the plasma stream which flows through the detection zone 3 and capture zone channel 6 reaches the capture antibody line 7. There is little or no labelled antibody/antigen trapped in the detection zone 3 as in the prior art constructions. Instead there is rapid and efficient capillary flow of the fluid from the detection zone 3 to the capture channel zone 6. The capture antibody 7 reacts with and concentrates the labelled antibody/analyte complex to form the detectable product with maximum efficiency. One advantageous result of this novel configuration is that the size of the diagnostic device can be reduced to a minimum.

Any of a variety of labels available to the skilled artisan may be utilized in the devices of this invention. Metal and enzyme labels are preferred. Metal labels are especially preferred due to their remarkable sensitivity. Amongst the metals, gold is most preferred principally because it is so widely employed for this type of reaction and its characteristics are so well understood. Additionally, a gold signal can be enhanced to become readily visible by the use of a soluble silver salt and a reducing agent in accordance with known procedures. The gold label acts as a catalyst to reduce the silver salt to metallic silver, which deposits as a visible product. A typical reactive pair is silver lactate, which serves as the source of reducible silver ions, and hydroquinone as a reducing agent. The metallic silver forms a readily discernible black deposit around each particle of gold.

The preferred particle size for gold labelled antibodies used in the invention is from about 35 to 65 nm, although appreciable variation can be tolerated depending on well understood factors such as the concentration of the analyte and the affinity of the reactants.

If an enzyme label such as horseradish peroxidase is employed, reaction may be detected by the addition of hydrogen peroxide and a dye such as ortho phenylenediamine in accordance with standard procedures.

There may be a preincubation zone in the detection zone although it is not a necessary feature of the invention. The preincubation zone is employed to remove products present in the blood which may interfere with the desired reactions or make them difficult to detect. For example, if the device is to be used to detect cardiac analytes a typical interferant is the isoform of creatine kinase, CK-MM. Antibodies to the isoform CK-MB may cross react with CK-MM and give false readings. This can be avoided by providing sufficient immobilized antibody to CK-MM in a preincubation zone upstream of the mobile antibody for CK-MB so that all of the CK-MM is removed before the moving sample reaches the detection antibody.

The device of FIG. 12 may utilize one or a plurality of labelled detector antibodies and capture antibodies in immobilized capture antibody lines. When several labelled detectors are employed care must be exercised to avoid interfering cross reactions. It is often best that the antibodies be arranged in more than one detection zone to react with their specific analytes as explained below in connection with the other figures.

Figure 13:
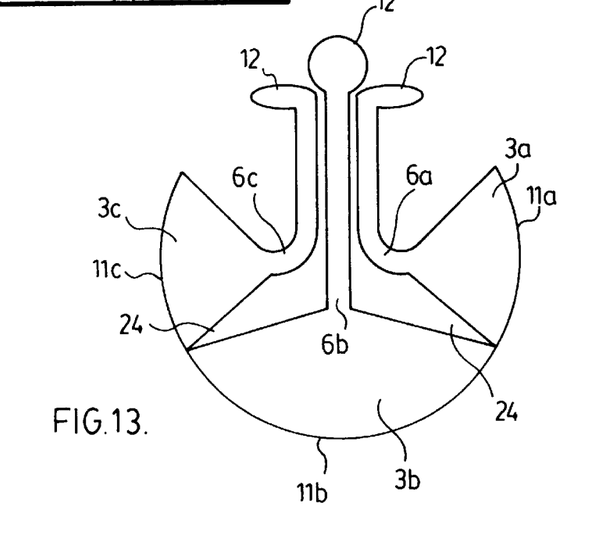

The device of FIGS. 12 and 13 may also be prepared to employ the biotin/avidin reaction utilizing variations such as those described above. In the presently preferred variation as applied to the device of FIG. 12, a biotin labelled antibody and a gold labelled antibody are movably placed in the detection zone 3, where each of them reacts with a different epitope on the analyte to form a ternary complex composed of biotin labelled antibody/analyte/gold labelled antibody which moves by capillary action into and through the capture channel zone 6 where it reacts with avidin or streptavidin to concentrate and form a detectable reaction product.

Of course, the antibodies employed in this invention may be either monoclonal or polyclonal. Similarly equivalents of the biotin/avidin reaction can be employed. All of the reagents mentioned herein may be replaced with equivalents and are illustrative but not limitations of the invention.

The skilled artisan will recognize that any porous substrate that chromatographically separates red blood cells and plasma from whole blood may be employed in this invention. However, nitrocellulose is preferred because it is readily available at reasonable cost. Nitrocellulose has been employed in chromatography and related fields for so many years that scientists and technicians are familiar with its properties.

Commercially available nitrocellulose sheets can be readily formed into any selected formation with any selected configuration of channels.

The nitrocellulose membranes of the invention may be characterized as sponge-like with a plurality of interconnected micropores of various sizes and dimensions giving rise to capillary forces within the membrane. This permits the biological fluid under investigation to move along the selected pathway.

For the separation of plasma from red blood cells in the practice of this invention, the area, geometry and dimensions of the various devices are so selected that the desired reactions take place in preselected areas as the liquid sample moves along predesigned pathways. For cardiac diagnosis of whole blood, these areas are selected on the basis of the relative speeds of the fronts of the red blood cell stream and the plasma stream, the kinetics of the desired reactions, the affinity of the antibodies for their respective epitopes and other factors which are well known to the skilled artisan or readily determined by conventional testing procedures.

While a variety of nitrocellulose materials are available in various cell sizes, the presently preferred porous carriers are those which, if used as a filter, that is filtering particles from a liquid stream flowing vertically to the horizontal surface of the membrane, will prevent the passage of particles larger than from 3 to 12 um. In the practice of the invention, membranes with a pore size from about 3 to 12 um, preferably 3 to 8 um, are preferred. Some variation is possible. However, as the pore size decreases, the mobility of a fluid within the membrane decreases, thereby increasing the time required for diagnosis. If the pores are too large, the time of passage reduces with the result that the reactants are not in contact with each other for a sufficient period for the diagnostic reactions to occur, or to occur to such a limited extent that they do not provide the desired information.

Nitrocellulose membranes with supporting polyester or other films are commercially available. These are preferred for use in this invention since unsupported membranes tend to be quite fragile, susceptible to fracture and difficult to handle in a mass production environment. Moreover, the films are impervious to the flowing fluids so that they do not interfere with the flow of liquid samples through the chosen pathways of the devices of this invention. One such membrane is available to a variety of pore sizes from Gerber-membrane of Gerbershausen, Germany.

The antibodies employed in this invention are prepared by standard techniques. See for example, Falfre, Howe, Milstein et al., Nature Vol. 266, 7, 550–552, April 1977. The disclosure of this seminal article on the preparation of monoclonal antibodies is incorporated herein by reference.

Procedures for fixing antibodies to substrates such as nitrocellulose are known and usable in producing the devices of this invention. Nitrocellulose is an avid binder for proteins. Hence, the immobile capture antibody need only be applied into the capture zone in a predetermined area. The labelled detector antibody may be movably affixed to the membrane by first saturating the detector zone with another protein such as bovine serum albumin.

FIG. 13 shows the configuration of an alternate porous membrane with three fluid pathways, for use with three analytes. The configuration and operation of the membrane will be apparent from the explanation of the operation of the other devices.

Figure 14:
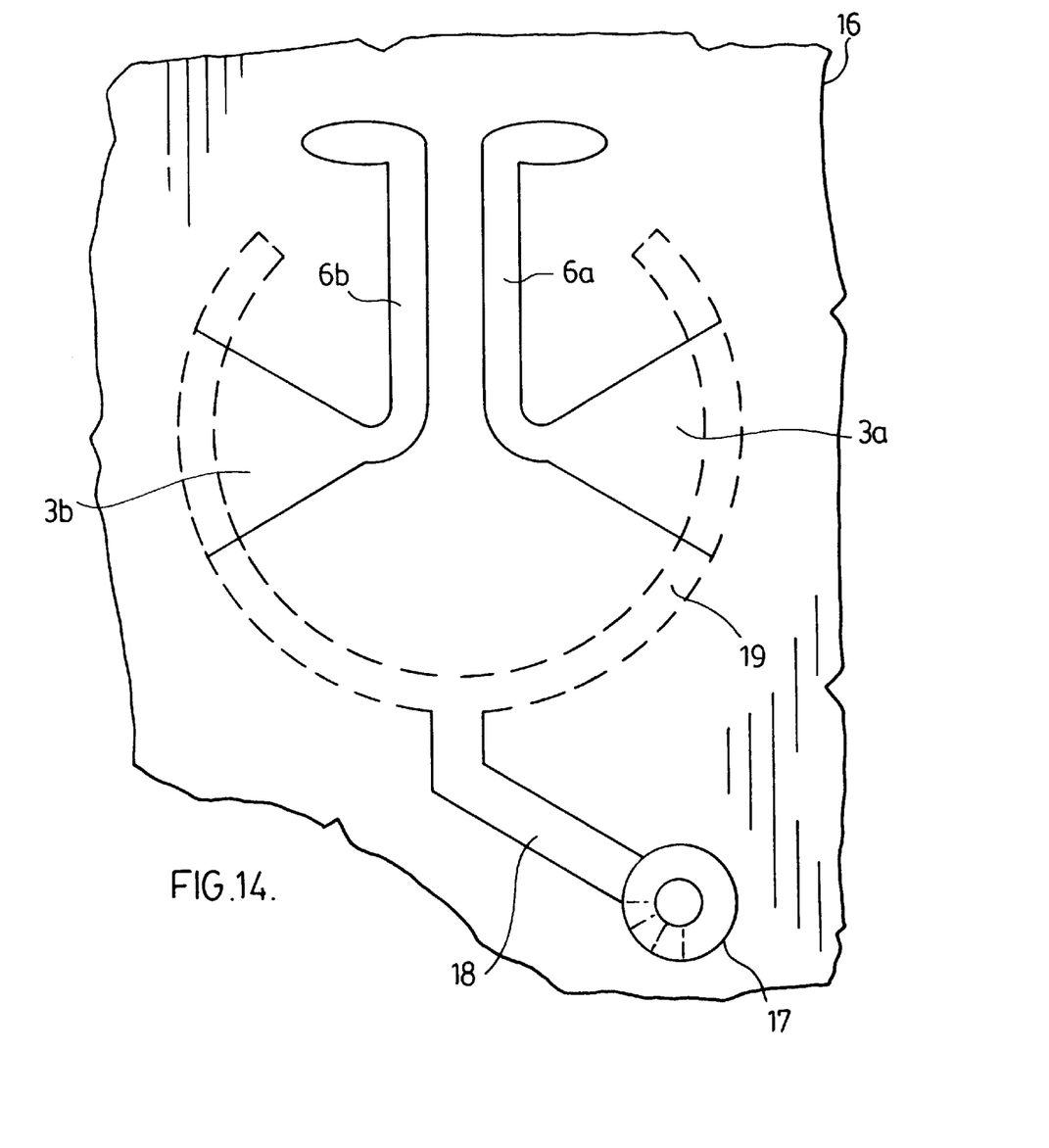
FIG. 14 shows an embodiment of the invention with two pathways and an arcuate circulation channel in a top layer.

FIG. 14 shows an embodiment of the invention with top layer 16 and the porous carrier thereunder, with two pathways for detecting two analytes, shown as detection zones 3a and 3b, and capture zone channels 6a and 6b, respectively, in the porous carrier layer. The arcuate circulation channel 19 in shown in the top layer 16. This device shows an opening 17, optionally beveled, in the top layer running from its top surface to the inner surface communicating with the shallow, narrow sample delivery channel 18, which then communicates with the sample circulation channel 19 formed in its bottom surface. The beveled opening is depicted further in FIGS. 15 and 16A, as described below.

Figure 15:
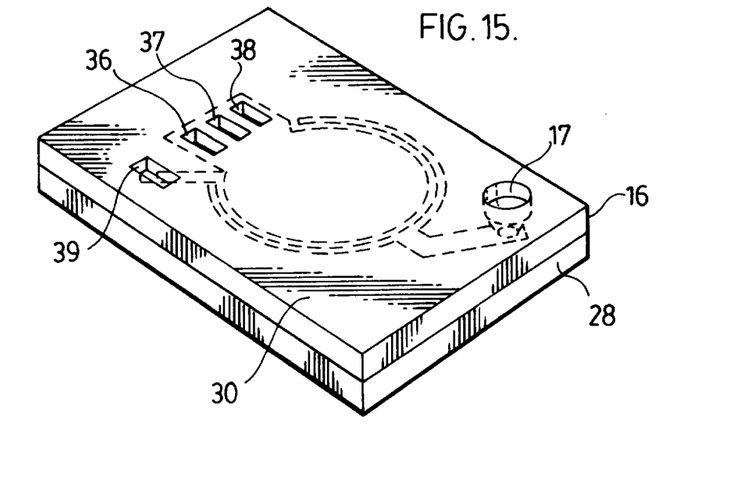
FIG. 15 is a perspective view of a device of the invention.
Figure 16A:
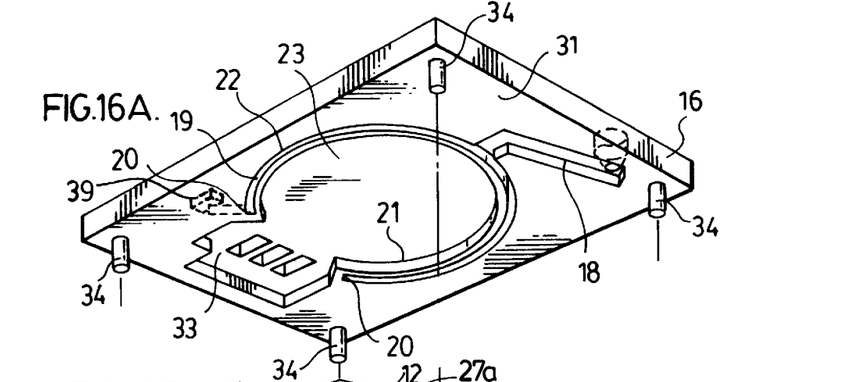
FIGS. 16A, 16B and 16C represent an exploded view of a device of the invention with a top member, a support member and a porous carrier in a configuration of FIG. 11.
Figures 16B, 16C:
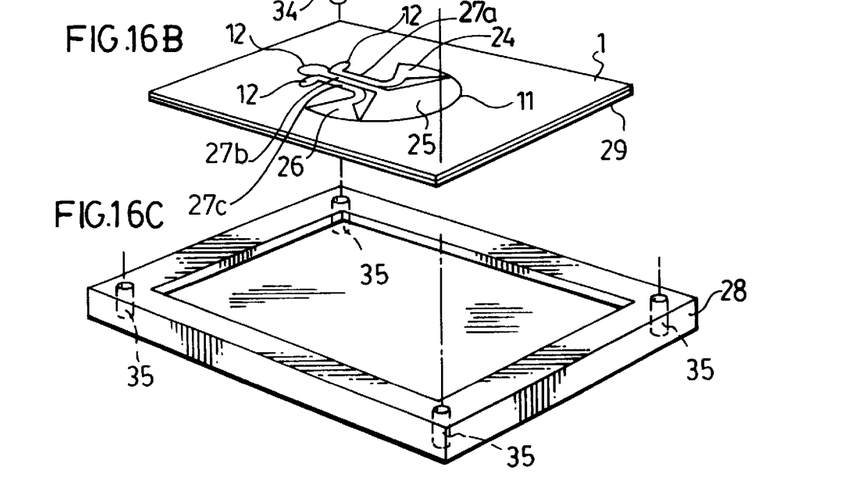

FIG. 15 is a perspective view and FIGS. 16A, 16B and 16C an exploded view of a device of the invention showing a top layer 16, a support layer 28, with a porous carrier 1 having a plastic backing layer 29 sandwiched between them. Through hole 17 runs from the upper surface 30 through to the bottom surface 31 in registry with a delivery channel 18 formed in the bottom surface 31 of the top layer 16.

Referring further to FIGS. 15 and 16, sample delivery channel 18 is in operative communication with circulation channel 19 also formed in the bottom surface 31 of top layer 16. The circulation channel 19 is closed at both ends as shown by numeral 20. The circulation channel 19 is formed with inner walls 21 and outer walls 22. As shown in FIG. 16a, inner walls 21 form the boundary of an indent formed in the bottom surface 31 of the top layer 16, referred to as capillary trap 23. Capillary trap 23 is shown extending into the area 33, but it is not necessary that it do so.

Referring to FIGS. 16A and 16B, top layer 16 is attached to the support layer 28 by pins 34 which may be force fit into corresponding holes 35. Any other equivalent means of attachment may be employed and the two layers 16 and 28 may be permanently or removably fixed.

Porous carrier 1 is shown in FIG. 16B with a backing 29 such as a polyester film. It is held between layers 16 and 28. The carrier 1 may have the same exterior dimensions as layers 16 and 28 so long as there is an operative pathway through which the fluid added by way of through hole 17 can pass through the delivery channel, the circulation channel, the detection zones and the capture zone channels to the closed ends 12 and 20, respectively, of the capture zone channels 27a, 27b, and 27c; and of circulation channel 19, respectively. The porous membrane 1 shown in FIG. 16C is configured similarly to the porous carrier of FIG. 11 for the detection of these analytes. Accordingly it contains three detection zones 24 25, and 26 communicating with three capture zone channels 27a, 27b and 27c, respectively. The arcuate border 11 of the detection zones extend over the inner walls 21 of circulation channel 19 so that the flow of fluid when stopped at ends 20 will flow by capillary action into the detection zones 24, 25 and 26.

The purpose of the capillary trap 23 now becomes apparent. If, in the absence of the capillary trap 23, the porous carrier 1 was in contact with a flat bottom surface of the top layer 16, the fluid in the circulation channel 19 would flow between that surface and porous carrier 1 rather than through the membrane in its preselected pathway from the through hole 17 to the ends of the capture zone channels.

The flow is stopped at the ends of the circulation channel to make it possible to control the size of the sample. An optional window 39 over an optional extension of the sample circulation channel shown as a dotted structure in FIGS. 15 and 16a, may be provided to indicate that adequate sample has been applied to fill the channel.

If the top layer 16 is transparent the formation of a visible reaction product will be readily apparent. If the top layer 16 is opaque it will be constructed with one or more viewing windows shown as 36, 37, 38. These windows as shown in FIG. 15 will be in registry with the capture zone channels so that the operator can view the formation of colored products or adjust an instrument such as a reflectometer to determine if a detectable reaction product has formed.

The device of FIG. 15 has three separate windows for purposes of illustration. In preferred devices, there will be one window extending transversely of the top surface 30 so that the results of all of the reactions can be viewed at once.

One of the advantages of this invention is that the devices whether intended to measure one, two or three antigens can have the same dimensions. Of course, the porous carrier layer 1 will be designed differently in each case. However, the top layer 16 does not require any changes to fit differently designed carrier layers 1.

The device of this invention can be readily manufactured by procedures already well known in the art.

The following non limiting examples are given by way of illustration only.

EXAMPLE 1

Whole Blood CK-MB Test

1A) On a polyester supported cellulose nitrate membrane (3 µm nominal pore size from Gerbermembrane GmbH, Gerbershausen, Germany) a contour as in FIG. 4 was drawn with a Paint Marker 751 yellow (from Edding AG, Ahrensburg, Germany). A capture line was prepared with a 13 mg/ml aqueous streptavidin solution (Streptavidin, poly, from Microcoat GmbH, Benried, Germany). A control line was prepared with a solution containing 80 µl of a 4% (w/v) solution of sucrose (from Sigma-Aldrich GmbH, Steinheim, Germany), 10 µl of water and 10 µl of a 1 mg/ml solution of recombinant CK-MB (from Spectral Diagnostics, Toronto, Canada). After drying the membrane was impregnated with a blocking solution containing in final concentrations: 0.06% (w/w) Octyl-beta-D-Gluco-pyranoside (from Fluka Chemie AG, Buchs, Switzerland), 1:30 dilution of Kasein-Bindemittel (from H. Schmineke & Co., Erkrath, Germany) and 30 mM 1,4-Piperazinediethanesulfonic acid (from Sigma-Aldrich GmbH, Steinheim, Germany) with a final pH of 6.2. After drying 2.7 µl of a gold-conjugate solution and 2 µl of a biotinylated antibody solution were applied and the membrane was dried again. The gold-conjugate solution and 2 µl of a biotinylated antibody solution were applied and the membrane was dried again. The gold-conjugate solution was prepared with a 40 nm gold sol loaded with 22 µg/ml of the antibody 5CKMB-6 from Spectral Diagnostics, Toronto, at an OD (520 nm) of 10 prepared by British Biocell International, Cardiff, UK. To 45 µl of this gold-conjugate (OD 10) 45 µl of water and 10 µl of a 2.5% (w/v) aqueous solution of Crotein C (from Croda Chemicals Ltd., UK) was added and mixed. The biotinylated antibody solution was prepared with the antibody 1rCKMB-28 from Spectral Diagnostics, Toronto as described to 57 µl of water 20 µl of a 6% (w/v) aqueous solution of Crotein C and 3 µl of a 2 mg/ml stock solution of the biotinylated antibody solution were added and mixed.

1B) For comparison, tests were prepared as in 1A) but without the biotinylated antibody solution, and instead of the streptavidin capture line an antibody capture line was prepared with the antibody 1rCKMB-28 (from Spectral Diagnostics, Toronto) at a concentration of 13 mg/ml.

Heparinized whole blood was spiked with rCKMB at indicated concentrations and 28 µl were applied to the test. The results (within 6–7 min.) were as follows:

| rCKMB in ng/ml | Streptavidin-Capture | Antibody-Capture |
| --- | --- | --- |
| 0 | – | – |
| 5 | + | n.d. |
| 20 | ++ | n.d. |
| 80 | ++++ | + |

– = no visible signal line
++++ = strong signal line
n.d. = not determined (this test has not been done)

All control lines were positive

EXAMPLE 2

Comparison Semicircular to Rectangular CK-MB Test

To demonstrate the versatility of the concept the sample entry in a semicircular area (circle segment) (FIGS. 4 and 5) was compared with a sample entry in a rectangular configuration, i.e. from 3 sides (FIGS. 9 and 10). The test areas (contour areas) are in both cases the same. Beside the contour shape and blood entry directions all other procedures were as in example 1A).

| rCKMB | circle segment | | rectangular | |
| --- | --- | --- | --- | --- |
| in ng/ml | signal | test time | signal | test time |
| 0 | – | 6.5 min. | – | 7.5 min. |
| 20 | ++ | 7.0 min. | ++ | 7.5 min. |

EXAMPLE 3

Semicircular Area—Three Analytes—One Detection Zone

A test as in example 1B) was prepared, but in addition to the CKMB antibody capture line there was a TNI antibody capture line and a Myoglobin antibody capture line.
TNI capture: 13 mg/ml polyclonal goat TNI
CKMB capture: 13 mg/ml 1rCKMB-28
Myoglobin capture: 13 mg/ml polyclonal rabbit Myoglobin
All antibodies were from Spectral Diagnostics, Toronto.
Gold-conjugates for the 3 analytes were from British Biocell Intern., Cardiff, UK:
TNI-gold-a: 40 nm gold sol loaded with 8 µg/ml 81-7 antibody (OD 10)
TNI-gold-b: 40 nm gold sol loaded with 16 µg/ml 21-14 antibody (OD 10)
Myoglobin-gold: 15 nm loaded with 90 µg/ml 2 Mb-295 antibody (OD 10)
CKMB-gold: 40 nm gold sol loaded with 22 µg/ml 5CKMB-6 (OD 10)
All antibodies were from Spectral Diagnostics, Toronto
The TNI gold conjugate solution contained: 15 µl of TNI-gold-a at an OD of 33, 30 µl of TNI-gold-b at an OD of 33, 45 µl water and 10 µl of a 2.5% (w/v) aqueous solution of Crotein C. 2.7 µl of this solution was applied to the test area.
The CKMB/Myoglobin gold conjugate solution contained: 48 µl of CKMB-gold at an OD of 33, 25 µl of Myoglobin-gold at an OD of 6, 17 µl water and 10 µl of a 2.5% aqueous solution of Crotein C. 2 µl of this solution was applied to the test area.
Heparinized whole blood was spiked with rCKMB, TNI and Myoglobin at indicated concentrations, and 28 µl were applied to the test. The results were as follows:

| | Signal | | |
| --- | --- | --- | --- |
| | TNI-capture | CKMB-capture | Myoglobin-capture |
| 0 ng/ml TM | – | | |
| 0 ng/ml CKMB | | – | |
| 0 ng/ml Myoglobin | | | trace |
| 2 ng/ml TNI | + | | |
| 20 ng/ml CKMB | | + | |
| 200 ng/ml Myoglobin | | | ++ |

Trace: even unspiked blood from a healthy subject can contain trace amounts of myoglobin

EXAMPLE 4

Semicircular Area—Three Analytes—Three Detection Zones

For more than one analyte with high sensitivity a contour as in FIG. 11 is used. The capture lines are done with streptavidin (13 mg/ml) as in Example 1A (the blocking procedure likewise). In this example the contour is drawn with Paint Marker 780 white (from Edding AG, Ahrensburg, Germany).

All gold sol-conjugates were prepared by British Biocell International, Cardiff, UK. All antibodies were from Spectral Diagnostics, Toronto.

TNI-gold conjugate: The following solutions were mixed: 18 μl gold conjugate A with an OD of 55 (50 nm gold sol loaded with 18 μg/ml of the antibody 81-7 at OD 10), 36 μl gold conjugate B with an OD of 55 (60 nm gold sol loaded with 10 μg/ml of the antibody 21-14 at OD 10), 36 μl water and 10 μl of a 2.5% (w/v) aqueous solution of Crotein C. 1.8 μl was applied to the test area.

Biotinylated TNI-antibodies: The following solutions were mixed: 67 μl water, 25 μl of a 6% (w/v) aqueous solution of Crotein C, 3.5 μl of a 1 mg/ml stock solution of biotinylated goat TNI antibodies and 5 μl of a 27.6 mg/ml solution of Chrom Pure Goat IgG (from Jackson Immuno Research Laboratories Inc.). 2.1 μl of this solution was applied to the test area.

CKMB-gold conjugate: As in example 1A), except that the OD of the stock solution was 33, and 1.1 μl of the mixture was applied.

Biotinylated CKMB-antibodies: As in example 1A), except that 1.4 μl was applied.

Myoglobin-gold conjugate: The following solutions were mixed: 17 μl of a gold conjugate with an OD of 6 (15 nm gold sol loaded with 90 μg/ml of the antibody 2 Mb-295 at OD 10), 73 μl water and 10 μl of a 2.5% (w/v) aqueous solution of Crotein C. 0.8 μl of this mixture was applied to the test.

Biotinylated Myoglobin-antibodies: The following solutions were mixed: 45 μl water, 25 μl of a 6% (w/v) aqueous solution of Crotein C and 30 μl of a 1 mg/ml stock solution of biotinylated rabbit antibodies Myoglobin. 0.5 μl of this mixture was applied to the test.

Heparinized whole blood was spiked with rCKMB, TNI and Myoglobin at indicated concentrations, and 70 μl was applied to the test.

The results (within 10 to 12 min.) were as follows:

|  | Signal | | |
| --- | --- | --- | --- |
|  | TNI | CKMB | Myoglobin |
| 0 ng/ml TNI | – | | |
| 0 ng/ml CKMB | | – | |
| 0 ng/ml Myoglobin | | | – |
| 2 ng/ml TNI | ++ | | |
| 20 ng/ml CKMB | | ++ | |
| 200 ng/ml Myoglobin | | | ++ |
| 10 ng/ml TNI | ++++ | | |
| 100 ng/ml CKMB | | ++++ | |
| 700 ng/ml Myoglobin | | | ++++ |

It is to be understood that the invention is not limited to the illustrations described and shown herein which are deemed to be merely illustrative of the best modes of carrying out the invention and which are susceptible of modifications of form, size, arrangement of parts and details of operation without departing from the spirit or scope of the invention. The invention, rather, is intended to encompass all such modifications which are within the spirit and scope of the claims.

What is claimed is:

1. An analytical test device for determining the presence of at least one analyte in a fluid sample, said device comprising:

a dry porous carrier;

at least one detection zone covering at least a segment of an area of said carrier;

a sample circulation channel in operative communication with said detection zone, the sample being permitted to enter from said sample circulation channel into said detection zone from a plurality of different directions;

at least one capture zone channel having an entrance end which is in operative communication with the detection zone to permit sample to flow from the detection zone into the capture zone channel, the distances between all points where the sample is permitted to enter the detection zone and said entrance end being essentially the same.

2. The device of claim 1 containing reagents required for reactions determinative of the analyte.

3. The device of claim 1 wherein said area is semicircular.

4. An analytical test device for determining the presence of at least one analyte in a fluid sample, said device comprising:

a dry porous carrier through which a sample can flow by capillary action;

a sample delivery means through which the sample can be applied to the device and flow thereinto;

a sample circulation channel which is closed at its terminal ends and which circumscribes an area of the carrier;

at least one detection zone covering at least a segment of said area of the carrier, wherein at least a segment of the sample circulation channel conforms with a border of the detection zone and is in operative communication with said detection zone, across which border the sample is permitted to enter into the detection zone simultaneously from a plurality of different directions and to form a stream flowing away from said border, the detection zone containing at least one mobile, labelled specific binding reagent for the at least one analyte, which said at least one mobile, labelled specific binding reagent is capable of reacting with said at least one analyte to form at least one labelled complex which is capable of moving along with said stream; and at least one capture zone channel having an entrance end and a closed terminal end, the entrance end being in operative communication with the detection zone to permit said stream to flow from the detection zone into the capture zone channel, the distances between all points of said border and said entrance end being essentially the same, the capture zone channel containing at least one immobilized specific binding reagent, which at least one immobilized specific binding reagent is capable of reacting with and concentrating said at least one labelled complex to form at least one detectable reaction product.

5. The device of claim 1 or 4 wherein the analyte is selected from troponin I, troponin T, myoglobin, CK-MB and mixtures thereof.

6. The device of claim 1 or 4 wherein the analyte is selected from hCG, LH and mixtures thereof.

7. The device of claim 1 or 4 wherein the fluid sample is selected from whole blood, plasma, serum and urine.

8. The device of claim 1 or 4 wherein the dry porous carrier is nitrocellulose.

9. The device of claim 1 or 4 comprising two or more detection zones arranged on said area of the carrier, there being an equal number of capture zone channels, each in operative communication with a corresponding detection zone.

10. The device of claim 4 wherein the sample circulation channel is arcuate and said area is semicircular.

11. The device of claim 1 or 4 wherein said area is polygonal or forms part of a polygon.

12. The device of claim 11 wherein said area is rectangular or forms part of a rectangle.

13. The device of claim 4 wherein said sample circulation channel is polygonal or forms part of a polygon.

14. The device of claim 13 wherein said sample circulation channel is rectangular or forms part of a rectangle.

15. The analytical test device of claim 4 suitable for determining the presence of at least one analyte contained in a liquid sample while permitting rapid and efficient flow of the sample through at least one defined pathway in which reactions determinative of the analyte take place, said device comprising:

a top support layer and a bottom support layer, the top support layer having an upper surface and a lower surface, the upper surface being formed with a through hole for the addition of the sample, the through hole being in registry with a sample delivery channel formed in the lower surface of the top layer and in operative communication with a sample circulation channel closed at its terminal ends and formed with inner and outer walls to define a pathway for the sample in the lower surface of the top layer, the inner walls of the sample circulation channel defining an indent in the lower surface of the top layer;

the bottom support layer being attached to the top layer;

a dry porous carrier layer through which the sample can flow by capillary action sandwiched between the top support layer and the bottom support layer, the porous carrier layer being configured to contain at least one detection zone having a border in operative communication with a segment of the sample circulation channel and a second opposite end in operative communication with a capture zone channel having an entrance end and a closed terminal end thereby to provide a conduit through which the liquid sample may flow by capillary action from the sample circulation channel to the terminal end of the capture zone channel;

the sample delivery channel, sample circulation channel, detection zone and capture zone channel forming a defined pathway through which the liquid sample flows from the through hole to the terminal end of the capture channel;

there being at least one mobile, labelled reagent which will specifically react with the analyte in the detection zone to form a labelled complex which will move by capillary action into the capture zone channel; and there being immobilized reagent in the capture zone channel which will react with and concentrate the labelled complex to form a detectable reaction product.

16. The device of claim 15 in which the sample circulation channel is arcuate.

17. The device of claim 15 in which the liquid sample is selected from whole blood, plasma, serum and urine.

18. The device of claim 15 wherein the analyte is selected from troponin I, troponin T, myoglobin, CK-MB and mixtures thereof.

19. The device of claim 15 wherein the analyte is selected from hCG, LH and mixtures thereof.

20. The device of claim 15 wherein the upper layer is transparent and the detectable reaction product is visible.

21. The device of claim 15 wherein the upper layer is opaque and has a view window through which the detectable reaction product is visible.

22. The device of claim 15 wherein said at least one analyte is a cardiac analyte and said liquid sample is whole blood containing red blood cells and plasma, the dry porous carrier causing said red blood cells to separate chromatographically from the plasma to provide a plasma front moving in the capture zone channel and a red blood cell front upstream thereof, a detectable portion of the labelled complex being between the red blood cell front and the plasma front so that the labelled complex is substantially free of red blood cells when said labeled complex is captured in the capture channel by reaction with the immobilized reagent.

23. The device of claim 22 wherein the mobile reagent in the detection zone is a labelled antibody which will react with one epitope on the analyte and the immobilized reagent is an antibody which will react with another epitope on the analyte.

24. The device of claim 22 wherein, in the detection zone, there is a mixture of a mobile labelled antibody which will react with one epitope on the analyte and a mobile biotin labelled antibody which will react with another epitope on the analyte, and immobilized reagent is an avidin.

25. The device of claim 22 containing one defined pathway for determining the presence of troponin I or troponin T.

26. The device of claim 22 containing two defined pathways, one for determining the presence of myoglobin, the other for determining the presence of CK-MB.

27. The device of claim 22 containing three defined pathways, the first pathway for determining the presence of troponin I or troponin T, the second pathway for determining the presence of myoglobin and the third pathway for determining the presence of CK-MB.

28. The device of claim 27 containing one defined pathway for determining the presence of troponin I.

29. The device of claim 22 in which there is only one defined pathway and it contains the reagents for determining the presence of myoglobin and CK-MB.

30. The device of claim 22 containing one defined pathway for determining the presence of troponin I or troponin T, the presence of myoglobin and the presence of CK-MB.

31. The device of claim 15 wherein, in the detection zone, there is a mixture of a mobile labelled antibody which will react with one epitope on the analyte and a mobile biotin labelled antibody which will react with another epitope on the analyte, and the immobilized reagent is selected from the group consisting of streptavidin and avidin.

32. The device of claim 15 wherein the label is a particulate direct label.

33. The device of claim 32 wherein the label is a gold label.

34. The device of claim 15 in which the dry porous carrier is nitrocellulose.

35. The device of claim 15 wherein said area is polygonal or forms part of a polygon.

36. The device of claim 35 wherein said area is rectangular or forms part of a rectangle.

37. A method for determining the presence of at least one analyte in a fluid sample comprising the sequential steps of:

i) providing an analytical test device suitable for determining the presence of at least one analyte contained in a liquid sample while permitting rapid and efficient flow of the sample through at least one defined pathway in which reactions determinative of the analyte take place, said device comprising:

a) a dry porous carrier through which sample can flow by capillary action;

b) at least one detection zone covering at least a segment of an area of said carrier, and a sample circulation channel in operative communication with said detection zone, such that said sample is permitted to enter from said sample circulation channel into said detection zone from a plurality of different directions, and said detection zone containing at least one mobile, labelled binding reagent for said at least one analyte, which mobile, labelled binding reagent is capable of reacting with said analyte to form a labelled complex;

c) at least one capture zone channel having an entrance end which is in operative communication with the detection zone to permit sample to flow from the detection zone into the capture zone channel, the distances between all points where said sample is permitted to enter said detection zone and said entrance end being essentially the same, said capture zone channel containing at least one immobilized specific binding reagent, which immobilized specific binding reagent is capable of reacting and concentrating said labelled complex to form a detectable reaction product;

ii) applying a quantity of said fluid sample to said detection zone;

iii) permitting the fluid sample to flow from the detection zone from said plurality of different directions to the capture zone channel and any said analyte therein to form a detectable reaction product at said immobilized specific binding reagent in said capture zone channel; and iv) identifying the presence of said at least one analyte in said fluid sample by detecting said detectable reaction product at said immobilized specific binding reagent in said capture zone channel.

38. The method of claim 37 wherein said at least one analyte is a cardiac analyte.

39. The method of claim 38 wherein three defined pathways are provided for identifying the presence of troponin I or troponin T together with identifying the presence of myoglobin and CK-MB.

40. The method of claim 39 wherein there is only one defined pathway provided for identifying the presence of troponin I or troponin T together with identifying the presence of myoglobin and CK-MB.

41. An analytical test device for determining the presence of at least one analyte in a fluid sample, said device comprising:

a dry porous carrier;

at least one detection zone covering at least a segment of an area of said carrier;

a sample circulation channel in operative communication with said detection zone, the sample being permitted to enter from said sample circulation channel into said detection zone from a plurality of different directions;

at least one capture zone channel having an entrance end which is in operative communication with the detection zone to permit sample to flow from the detection zone into the capture zone channel.

42. The device of claim 41 wherein said area is polygonal or forms part of a polygon.

43. The device of claim 42 wherein said area is rectangular of forms part of a rectangle.

44. An analytical test device suitable for determining the presence of at least one analyte contained in a liquid sample while permitting rapid and efficient flow of the sample through at least one defined pathway in which reactions determinative of the analyte take place, said device comprising:

a dry porous carrier through which a sample can flow by capillary action;

a sample delivery means through which the sample can be applied to the device and flow thereinto;

a sample circulation channel in operative communication with said sample delivery means, which is closed at its terminal ends and which circumscribes an area of the carrier;

at least one detection zone covering at least a segment of said area of the carrier, wherein at least a segment of the sample circulation channel conforms with a border of the detection zone and is in operative communication with said detection zone, across which border the sample is permitted to enter into the detection zone simultaneously from a plurality of different directions and to form a stream flowing away from said border, the detection zone containing at least one mobile, labelled specific binding reagent for the at least one analyte, which said at least one binding reagent is capable of reacting with said at least one analyte to form at least one labelled complex which is capable of moving along with said stream; and at least one capture zone channel having an entrance end and a closed terminal end, the entrance end being in operative communication with the detection zone to permit said stream to flow from the detection zone into the capture zone channel, the capture zone channel containing at least one immobilized specific binding reagent, which at least one binding reagent is capable of reacting with and concentrating said at least one labelled complex to form at least one detectable reaction product.

45. The device of claim 44 wherein said sample circulation channel is polygonal or forms part of a polygon.

46. The device of claim 45 wherein said sample circulation channel is rectangular or forms part of a rectangle.

47. The device of claim 46 wherein the analyte is selected from troponin I, troponin T, myoglobin, CK-MB and mixtures thereof.

48. The device of claim 46 wherein the fluid sample is selected from whole blood, plasma, serum and urine.

49. The device of claim 46 wherein the dry porous carrier is nitrocellulose.

50. The device of claim 46 comprising two or more defined pathways, each pathway comprising a detection zone arranged on said area of the carrier, and a capture zone channel in operative communication with said detection zone.

51. The device of claim 46 wherein the label is a gold label.

52. The device of claim 46 wherein, in the detection zone, there is a mixture of a mobile labeled antibody which will react with one epitope on the analyte and a mobile biotin labelled antibody which will react with another epitope on the analyte, and the immobilized reagent is selected from the group consisting of streptavidin and avidin.

53. The device of claim 46 containing two defined pathways, one for determining the presence of myoglobin, the other for determining the presence of CK-MB.

54. The device of claim 46 containing three defined pathways, the first pathway for determining the presence of troponin I or troponin T, the second pathway for determining the presence of myoglobin and the third pathway for determining the presence of CK-MB.

55. The device of claim 46 wherein said at least one analyte is a cardiac analyte and said liquid sample is whole blood containing red blood cells and plasma, the dry porous carrier causing said red blood cells to separate chromatographically from the plasma to provide a plasma front moving in the capture zone channel and a red blood cell front upstream thereof, a detectable portion of the labelled complex being between the red blood cell front and the plasma front so that the labelled complex is substantially free of red blood cells when said labeled complex is captured in the capture channel.

56. The device of claim 55 wherein the mobile reagent in the detection zone is a labelled antibody which will react with one epitope on the analyte and the immobilized reagent is an antibody which will react with another epitope on the analyte.

57. The device of claim 55 wherein, in the detection zone, there is a mixture of a mobile labelled antibody which will react with one epitope on the analyte and a mobile biotin labelled antibody which will react with another epitope on the analyte, and the immobilized reagent is an avidin.

58. The device of claim 55 containing one defined pathway for determining the presence of troponin I or troponin T.

59. The device of claim 55 containing two defined pathways, one for determining the presence of myoglobin, the other for determining the presence of CK-MB.

60. The device of claim 55 containing three defined pathways, the first pathway for determining the presence of troponin I or troponin T, the second pathway for determining the presence of myoglobin and the third pathway for determining the presence of CK-MB.

61. The device of claim 60 containing one defined pathway for determining the presence of troponin I.

62. The device of claim 55 containing one defined pathway for determining the presence of troponin I or troponin T, the presence of myoglobin and the presence of CK-MB.

63. The device of claim 62 containing one defined pathway for determining the presence of troponin I, the presence of myoglobin and the presence of CK-MB.

64. An analytical test device suitable for determining the presence of at least one analyte contained in a liquid sample while permitting rapid and efficient flow of the sample through at least one defined pathway in which reactions determinative of the analyte take place, said device comprising:

a dry porous carrier through which a sample can flow by capillary action;

a sample delivery means through which the sample can be applied to the device and flow thereinto;

a sample circulation channel in operative communication with said sample delivery means, which is closed at its terminal ends and which circumscribes an area of the carrier, said sample circulation channel being polygonal or forming part of a polygon;

at least one detection zone covering at least a segment of said area of the carrier, wherein at least a segment of the sample circulation channel conforms with a border of the detection zone and is in operative communication with said detection zone, across which border the sample is permitted to enter into the detection zone simultaneously from a plurality of different directions and to form a stream flowing away from said border, the detection zone containing at least one mobile, labelled specific binding reagent for the at least one analyte, which said at least one binding reagent is capable of reacting with said at least one analyte to form at least one labelled complex which is capable of moving along with said stream; and at least one capture zone channel having an entrance end and a closed terminal end, the entrance end being in operative communication with the detection zone to permit said stream to flow from the detection zone into the capture zone channel, the capture zone channel containing at least one immobilized specific binding reagent, which at least one binding reagent is capable of reacting with and concentrating said at least one labelled complex to form at least one detectable reaction product.

65. The device of claim 64 wherein said sample circulation channel is rectangular or forms part of a rectangle.

66. The device of claim 64 containing one defined pathway for determining the presence of troponin I, the presence of myoglobin and the presence of CK-MB.

67. The device of claim 64 wherein the dry porous carrier is nitrocellulose.

68. The device of claim 64 wherein the fluid sample is whole blood.

69. The device of claim 64 wherein, in the detection zone, there is a mixture of a mobile labeled antibody which will react with one epitope on the analyte and a mobile biotin labelled antibody which will react with another epitope on the analyte, and the immobilized reagent is selected from the group consisting of streptavidin and avidin.

70. An analytical test device suitable for determining the presence of at least one analyte contained in a liquid sample while permitting rapid and efficient flow of the sample through at least one defined pathway in which reactions determinative of the analyte take place, said device comprising:

a dry porous carrier through which a sample can flow by capillary action;

a sample delivery means through which the sample can be applied to the device and flow thereinto;

a sample circulation channel in operative communication with said sample delivery means, which is closed at its terminal ends and which circumscribes an area of the carrier, said sample circulation channel being rectangular or forming part of a rectangle;

at least one detection zone covering at least a segment of said area of the carrier, wherein at least a segment of the sample circulation channel conforms with a border of the detection zone and is in operative communication with said detection zone, across which border the sample is permitted to enter into the detection zone simultaneously from a plurality of different directions and to form a stream flowing away from said border, the detection zone containing at least one mobile, labelled specific binding reagent for the at least one analyte, which said at least one binding reagent is capable of reacting with said at least one analyte to form at least one labelled complex which is capable of moving along with said stream; and at least one capture zone channel having an entrance end and a closed terminal end, the entrance end being in operative communication with the detection zone to permit said stream to flow from the detection zone into the capture zone channel, the capture zone channel containing at least one immobilized specific binding reagent, which at least one binding reagent is capable of reacting with and concentrating said at least one labelled complex to form at least one detectable reaction product.

* * * * *